(12) United States Patent
Youngner et al.

(10) Patent No.: US 8,928,879 B2
(45) Date of Patent: *Jan. 6, 2015

(54) DYNAMIC CODED FILTER GAS DETECTION

(75) Inventors: Daniel Youngner, Maple Grove, MN (US); Bernard S. Fritz, Eagan, MN (US); Yue Liu, Plymouth, MN (US); James A. Cox, New Brighton, MN (US)

(73) Assignee: Honeywell International Inc., Morristown, NJ (US)

( * ) Notice: Subject to any disclaimer, the term of this patent is extended or adjusted under 35 U.S.C. 154(b) by 279 days.

This patent is subject to a terminal disclaimer.

(21) Appl. No.: 13/484,005

(22) Filed: May 30, 2012

(65) Prior Publication Data

US 2012/0307239 A1 Dec. 6, 2012

Related U.S. Application Data

(60) Provisional application No. 61/493,624, filed on Jun. 6, 2011.

(51) Int. Cl.
| | | |
|---|---|---|
| *G01J 3/04* | (2006.01) | |
| *G01J 3/18* | (2006.01) | |
| *G01N 21/35* | (2014.01) | |
| *G01J 3/28* | (2006.01) | |
| *G01J 3/457* | (2006.01) | |
| *G01J 3/14* | (2006.01) | |
| *G01J 3/02* | (2006.01) | |
| *G01N 21/31* | (2006.01) | |

(52) U.S. Cl.
CPC ........... *G01J 3/14* (2013.01); *G01N 2021/3177* (2013.01); *G01J 3/1804* (2013.01); *G01N 21/3504* (2013.01); *G01J 3/2803* (2013.01); *G01J 3/457* (2013.01); *G01J 3/0229* (2013.01); *G01J 3/0208* (2013.01)
USPC ......................................................... 356/310

(58) Field of Classification Search
CPC .............. F24J 2/04; F24J 2/46; G01J 3/0208; G01J 3/0229; G01J 3/0237; G01J 3/14; G01J 3/1804; G01J 3/2803; G01J 3/457; G01J 3/453; Y02E 10/44; G01N 21/3504
USPC ............ 356/310, 401, 446; 359/199.1, 224.1, 359/290, 572, 566; 250/372, 373, 338.5, 250/343, 345
See application file for complete search history.

(56) References Cited

U.S. PATENT DOCUMENTS

| | | | |
|---|---|---|---|
| 5,450,193 A * | 9/1995 | Carlsen et al. | 356/301 |
| 6,356,350 B1 * | 3/2002 | Silver et al. | 356/437 |
| 6,872,947 B1 * | 3/2005 | Greywall | 250/339.13 |
| 7,420,673 B2 * | 9/2008 | Hagler | 356/310 |
| 2005/0061969 A1 * | 3/2005 | Greywall | 250/300 |
| 2006/0007438 A1 * | 1/2006 | Chen | 356/305 |
| 2008/0100836 A1 * | 5/2008 | Hagler | 356/310 |
| 2012/0307239 A1 * | 12/2012 | Youngner et al. | 356/310 |

* cited by examiner

*Primary Examiner* — Kara E Geisel
*Assistant Examiner* — Violeta A Prieto
(74) *Attorney, Agent, or Firm* — Schwegman Lundberg & Woessner, P.A.

(57) ABSTRACT

A device for detecting gas concentrations includes a movable coded filter. An optical element is positioned to receive gas filtered light and spectrally separate the gas filtered light. A photo detector is positioned to receive the spectrally separated light through slits in the moveable coded filter to provide an AC signal representative of a selected gas.

18 Claims, 12 Drawing Sheets

DYNAMIC CODED FILTER GAS DETECTION

RELATED APPLICATIONS

This application claims priority to U.S. Provisional Application Ser. No. 61/493,624 (entitled DYNAMIC EIGEN SPECTROSCOPY), filed Jun. 6, 2011), which application is incorporated herein by reference.

TECHNICAL FIELD

The present invention pertains to detecting gas concentrations and in particular detecting gas concentration using a dynamic coded filter.

BACKGROUND

There is a need in industry, in the Department of Defense (DOD), and in homes, factories, and offices to perform remote analysis of nearby chemicals. For example, it may be desired to monitor the atmospheric gasses in and around an oil refinery to determine whether hydrogen sulfide is present, and to quantify its concentration if it is detected. The Department of Defense may desire to monitor a gas cloud heading toward an Army base to determine whether that cloud contains chemical warfare agents. Existing techniques, including TDLS (Tunable Diode Laser Spectroscopy), NDIR (Non-Dispersive InfraRed analysis), Polychromatry, and FTIR (Fourier Transform InfraRed analysis) all have limitations that, depending on the application, can limit their ability to detect atmospheric gasses at the desired level.

There is a need by the DoD and by industrial safety personnel to be able to identify unknown chemical contaminant in the atmosphere from afar. The problem can be very difficult because normal components of the atmosphere such as $H_2O$ and $CO_2$ (water vapor and carbon dioxide) have spectral signatures that are similar to, and overlap with the spectral signature of many of the contaminants of interest.

SUMMARY

A device for detecting gas concentrations includes a movable coded filter. An optical element is positioned to receive gas filtered light and spectrally separate the gas filtered light. A photo detector is positioned to receive the spectrally separated light through slits in the moveable coded filter to provide an AC signal representative of a selected gas.

An alternative device for detecting gas concentrations includes a movable coded filter having multiple lanes of slits in a proof mass. An optical element is positioned to receive gas filtered light and spectrally separate the gas filtered light onto all lanes of the coded filter wherein spectral bands run in the same direction as the slits. The slits are positioned in each lane to cancel AC signals corresponding to at least one gas not of interest. A photo detector is positioned in each lane to receive the spectrally separated light through the oscillating slits in the moveable coded filter to provide an AC signal representative of a selected gas. A controller is coupled to receive the AC signal from each photodetector, convert the AC signal to a digital signal, and to correlate an amplitude of the AC signal to a concentration of the selected gas.

A method for detecting a gas includes receiving light from a light source through a plume of gas, spectrally separating the light onto one or more lanes of a coded filter, oscillating a coded filter to selectively pass portions of the spectrally separated light onto a single photo detector in each lane, and detecting an AC signal from each lane via the single photo detector representative of a gas of interest.

DETAILED DESCRIPTION

Figure 1:
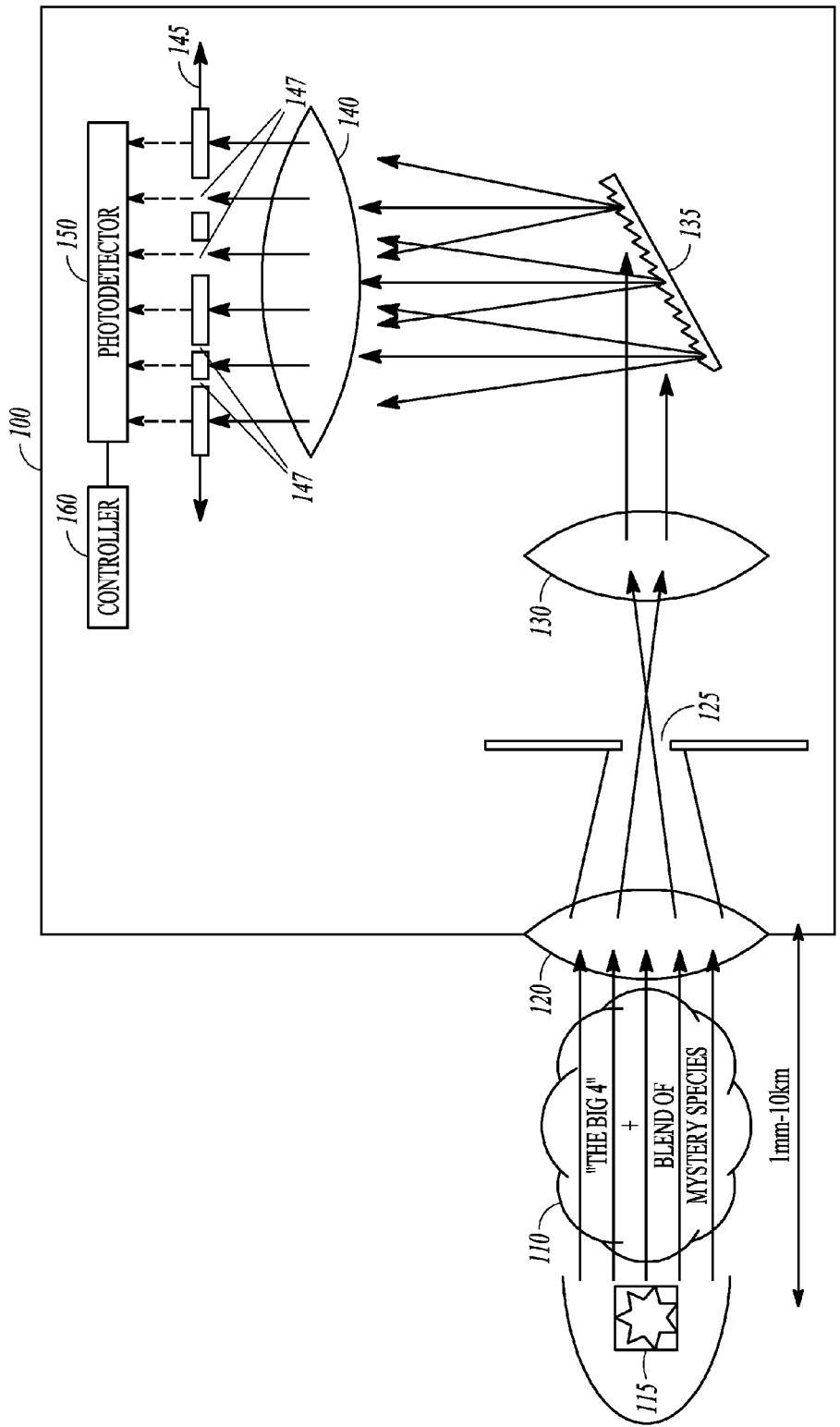
FIG. 1 is a block diagram of a device for detecting gas according to an example embodiment.

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

The functions or algorithms described herein may be implemented in software or a combination of software and human implemented procedures in one embodiment. The software may consist of computer executable instructions stored on computer readable media such as memory or other type of storage devices. Further, such functions correspond to modules, which are software stored on storage devices, hardware, firmware or any combination thereof. Multiple functions may be performed in one or more modules as desired, and the embodiments described are merely examples. The software may be executed on a digital signal processor, ASIC, microprocessor, or other type of processor operating on a computer system, such as a personal computer, server or other computer system.

A device receives light from a source of light after the light has passed through a gas. The gas absorbs some of the light depending on the constituents of the gas. Each gas has its own unique absorption spectra. The light reaching the device has its spectra spread out using an optical element, such as a prism or diffraction grating. The optical element spectrally separates incoming light so that shorter wavelengths are directed in one direction and longer wavelengths are directed in a second direction. An opaque filter with slits is then oscillated at a selected frequency, with the slits moving between different frequencies or wavelengths of the spread spectra.

A photo detector is positioned to receive the light passed by the slits in the filter to measure power of the total amount of light passed. The slits are designed and positioned to pass offseting AC components of the spectrally separated light passed by at least one not of interest gas, while allowing at least one AC component of the spectrally separated light from a selected gas to be received by the photo detector. The photo detector is responsive to the AC component or components of the selected gas to indicate the presence of the selected gas. The amplitude of an AC signal provided by the photo detector will be proportional to the amount of the selected gas that the light has passed through. This process may be referred to as DES (Dynamic Eigen Spectroscopy) due to the enhancement of the AC signal of the gas of interest while AC signals of gases not of interest cancel each other.

In some embodiments, multiple slits are utilized to cancel AC components from more than one gas, while allowing an AC component from a selected gas to be detected by the photo detector. The filter may include multiple lanes with different sets of slits to detect different gases. Each lane will also be associated with a different photo detector.

A method includes physically separating a received spectra by wavelength. This may be done using a diffraction grating or prism in various embodiments. The received spectra is dynamically changed so that the contribution to the total (dynamic or AC) signal from the particular spectral components of a gas of interest also change dynamically. The contribution to the (dynamic) signal from the not-of-interest species does not change. A detector is used to detect the resulting signal. The signal at the detector orthogonal to interferrents is effectively cancelled by movement of a filter having slits positioned to ensure that AC signals contributed by the not of interest species cancel each other.

When the spectra is separated by wavelength and collimated by using real diffraction gratings, prisms, and/or other optical elements, the spectra that reaches the coded filter will often be smeared relative to the spectra that arrives at the detector. This smear will often have a Gaussian shape, but may include linear and/or other components depending on the details of the optical elements, the separation of the optical elements, and the rotation of the slits relative to separation-axis of the spectrally-separated light. The coded filter is designed to take this spectral smear into account. In some cases it may be advantageous to deliberately induce a significant amount of spectral smear, thereby smoothing out sharp spectral peaks, and minimizing the sensitivity of the detector to red-blue misalignments of the spectral peaks relative to the slits in the coded filter.

In one embodiment, a set of many (e.g. 25) different coded filters, each of which is orthogonal to a known set of spectra (e.g. the spectra of water vapor, carbon dioxide, methane, and ozone) to cancel out signals from such gases. Each of these ~25 coded filters may be orthogonal and different from one another in a unique way. Each uses different portions of the spectrum to provide orthogonality. When the AC signal is measured from several of the coded filters, it becomes possible to determine the composition and the quantities of several of the chemicals that are in the atmosphere.

A schematic diagram of a system 100 for detecting gas is shown in FIG. 1. A gas 110 may contain many different gasses that absorb light from a source of light 115. The light source may be a blackbody that emits a spectrally broad source of light. Examples include background terrain that reflects sunlight, or an actual active source, such as a light emitting diode or other artificial source of light. Each different type of gas absorbs different wavelengths of light, while allowing other wavelengths to pass. The gas may operate as a sort of filter. The passed light is received by the system 100 via a lens 120 that directs the light toward a slit 125.

Light that proceeds through the slit is collimated by a lens 130 and then spectrally separated by an optical element 135, such as a prism or diffraction grating. The spectrally separated light is then collimated again via a lens 140 and directed toward a coded filter 145. The coded filter is opaque with multiple slits 147 positioned to allow different wavelengths of the spectrally separated light to pass to a photo detector 150. The slits are oriented parallel to the spectral lines and each extends a selected width of the spectra. The coded filter is oscillated transverse 155 to the spectrally separated light such that AC components of the spectrally separated light are incident on the photo detector 150. A controller 160 is coupled to the photo detector to receive a signal representative of the amplitude of the light incident on the photo detector 150. The controller may include an analog amplifier, an analog to digital converter, optional digital weighting functions, and a processor to process the digital signals derived from the photo detector 150 signal. In various embodiments, the controller may integrate the AC signals over a time period that may vary from 0.1 seconds giving a signal to noise ratio of approximately 3:1, to 10 seconds, providing a signal to noise ratio of approximately 30:1. The integration times and signal to noise ratios may vary significantly from embodiment to embodiment, with neither quoted times and ratios being limits.

Figure 2:
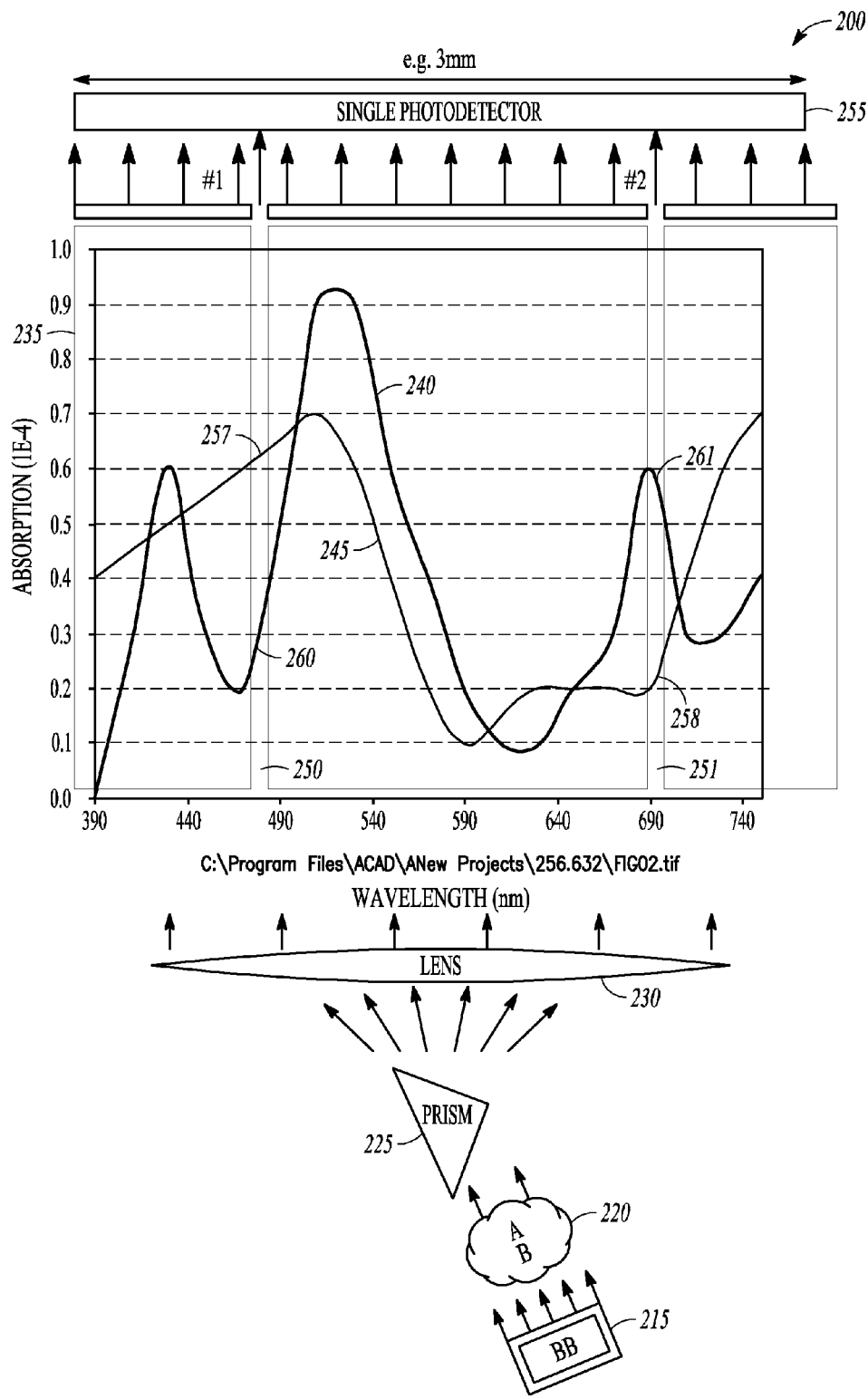
FIG. 2 is a schematic diagram of a two slit coded filter designed to detect a gas according to an example embodiment.

FIG. 2 is a schematic diagram of a two slit coded filter generally at 200. A light source is indicated at 215 that emits light toward a plume 220 of two gases, A and B. Light that is transmitted through the plume is spectrally separated by an optical elements 225, and collimated via a lens 230. A coded filter is represented at 235, which also illustrates the light absorbed from gases A and B at 240 and 245 respectively. In one embodiment, the filter reduces the total amount of light reaching a photo detector 255 by approximately 10×. Absorption is indicated on a vertical axis with numbers corresponding to absorption at $10^{-4}$, and the wavelength of the light is indicated on the horizontal axis in nanometers.

Two slits in the coded filter are indicated at 250 and 251 respectively. The slits are not necessarily to scale. Slit 250 is positioned to move about a portion of the spectra corresponding to gas 240 indicated at 257, and slit 251 is positioned about a portion of the spectra corresponding to gas 245 indicated at 258. The coded filter is then oscillated transverse to the spectra a selected distance, left and right as shown, about those portions of the spectra. Typical frequencies of oscillation are between 5 and 10 kHz, but may vary significantly in further embodiments. The oscillation of the coded filter results in the total amount of light reaching the photo detector being modulated at the oscillation frequency $f_0$. Note that both of the gas 245 spectra are increasing, resulting in AC signals from gas 245 that add. The signal scales linearly with the amount of gas 245. This signal will be detected by the photo detector 255, and passed on to the controller.

The same two slits 250 and 251 with respect to gas 245 correspond to portions 260 and 261 of the gas 240 spectra. Note that while the spectra is increasing at 260, it is decreasing at 261. The light passed by slits 250 and 251 from gas 240 counter each other. The resulting signals from these two areas of the gas 240 spectra effectively cancel each other out, resulting in a net zero AC signal reaching the photo detector 255.

Figure 3:
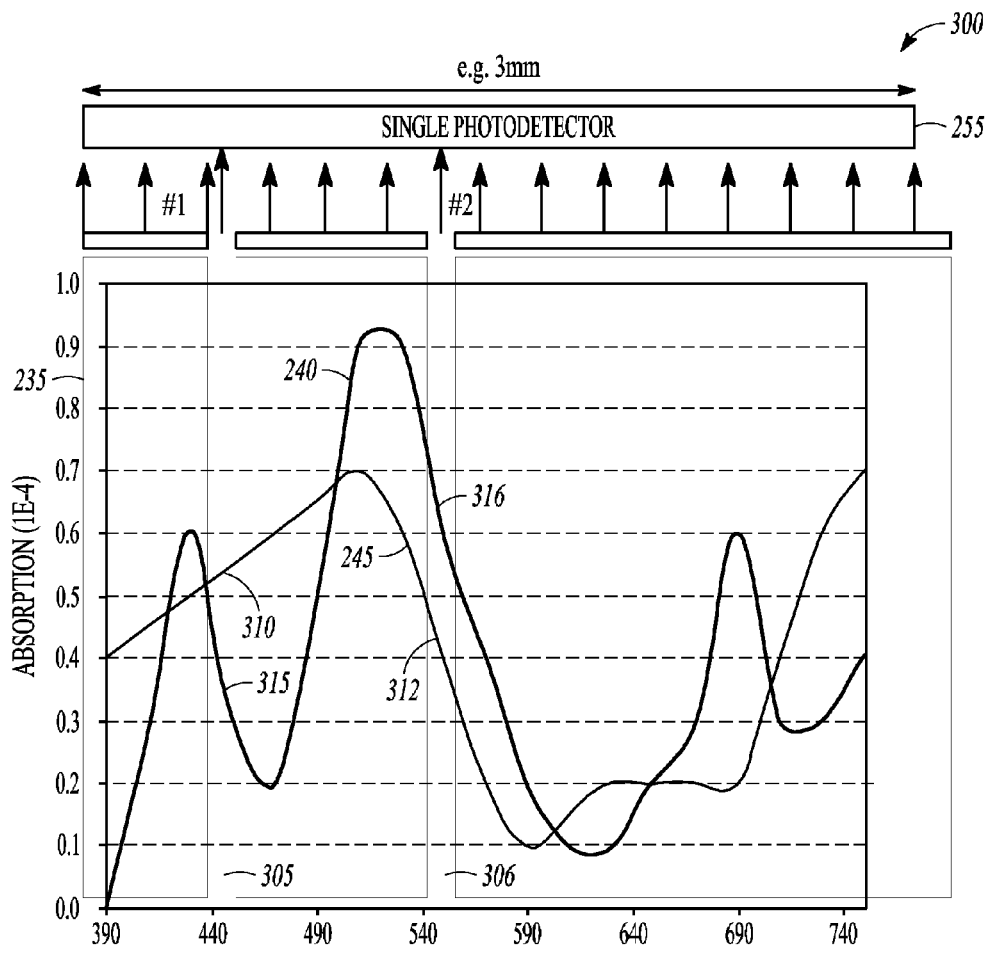
FIG. 3 is a schematic diagram of a two slit coded filter designed to detect a different gas according to an example embodiment.

FIG. 3 is a schematic diagram 300 of a two slit 305, 306 coded filter designed to detect gas 245. Slits 305, 306 pass light from gas 240 at 310 and 312 respectively. The slits 305, 306 are moved along the spectra compared to the slits in the previous coded filter in FIG. 2. Note that the spectra of gas 245 at 310 and 312 are increasing and decreasing respectively. Oscillation of the slits results in two AC signals to counter each other, resulting in minimal to no AC signal from the spectra of gas 245. Meanwhile, the corresponding spectra from gas 240 indicated at 315 and 316 are both decreasing, adding to each other.

Figure 4:
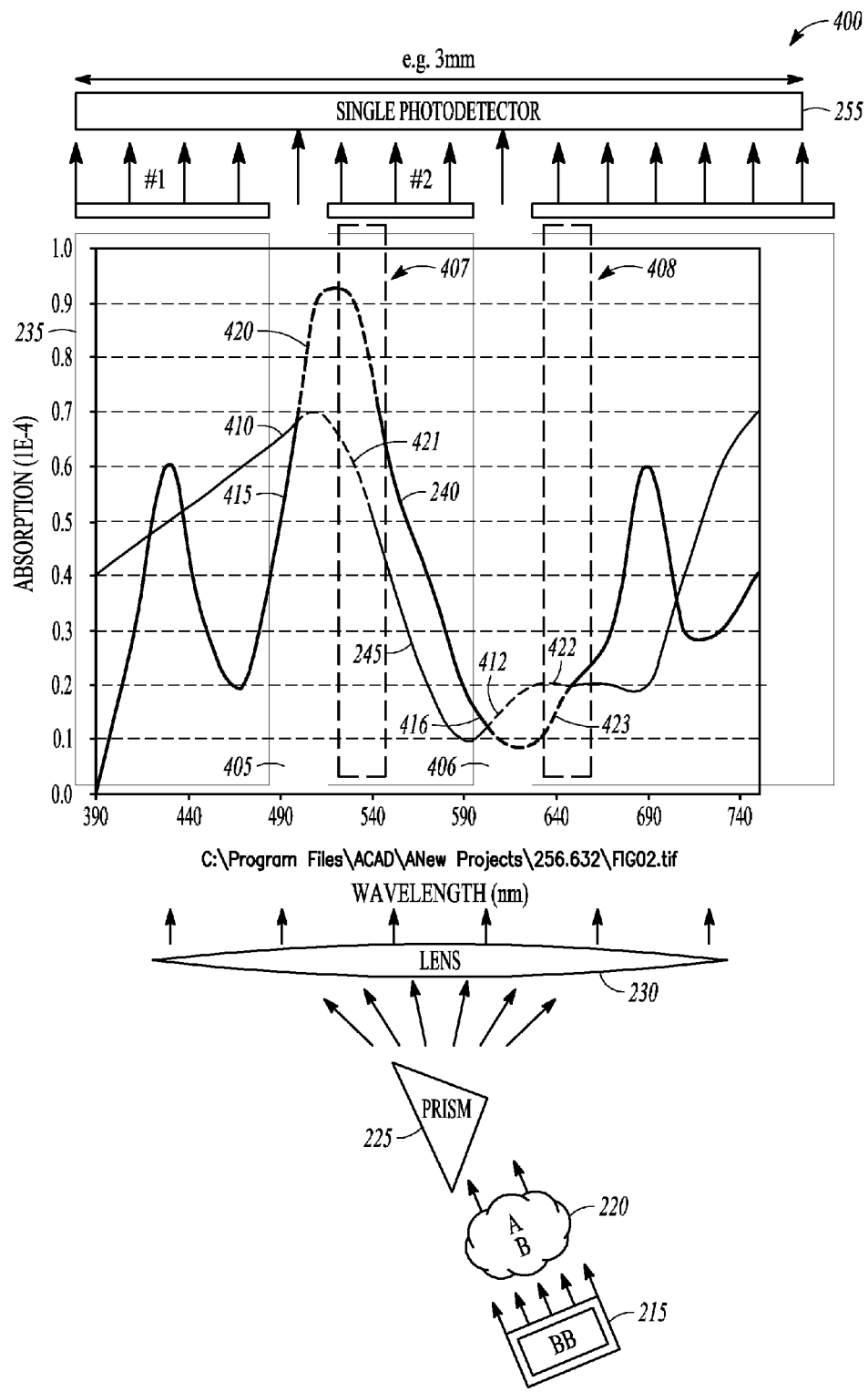
FIG. 4 is a schematic diagram of an alternative two slit coded filter designed to detect a gas according to an example embodiment.

FIG. 4 is a schematic diagram 400 of a two slit 405, 406 coded filter designed to detect gas 240. Slits 405, 406 pass light from gas 240 at 410 and 412 respectively. The slits 405, 406 are moved along the spectra to positions indicated by rectangles labeled as 407 and 408. Note that the spectra of gas 245 at 410 and 412 are both changing in the same manner. These portions of the spectra are labeled 421 and 422 respectively and shown as broken lines. Both portions of the spectra have downward curvature, or negative $2^{nd}$ derivatives. As the coded filter moves back and forth at oscillation frequency $f_0$, both portions of the signal from slit 405, 407 and slit 406, 408 add together to produce a strong signal at the photodetector with frequency $2f_0$. Meanwhile, the spectra from gas 245 has a negative $2^{nd}$ derivative (downward curvature) in slit 405 and a positive $2^{nd}$ derivative (positive curvature) in slit 406. As the coded filter moves back and forth between positions 405, 406 and positions 407, 408, the $2f_0$ component of the signal from gas 240 from slit 405, 407 will be negative whereas the $2f_0$ component of the signal from gas 240 from slit 406, 408 will be positive. If the slit widths are adjusted properly the two $2f_0$ components of the signal from gas 245 will exactly cancel one another, resulting in no net contribution to the $2f_0$ signal from gas 240. If both gases 240 and 240 are present at the same time, the $2f_0$ signal will be directly proportional to the concentration of gas 245, but independent of the concentration of gas 240.

Different weight functions may be used to compensate for many different deviations in devices from a nominal design point. These may include one or more of the following. Drive the comb resonator at $\omega_0$; sense at $\omega_0$, and add appropriately weighted harmonics to the sense function.

When designing the coded filter, it is the designer's prerogative to position the slits so that spectra "A" and spectra "B" have different radii of curvature ($2^{nd}$ derivatives) at at least one slit. Adding a $k_2 \sin(2\omega_0)$ component to the weighting function enables exploitation of the different radii of curvature.

Weighting may also be done by adjusting slit widths a-priori to deal with known non-flatness in detector sensitivity and source emissivity.

In further embodiments, higher harmonic $k_n \sin(n\omega_0)$ terms may be added to the weighting function as needed to deal with variabilities in the absorption spectra in the different chemicals.

The Absorption function $A_{CS}$ for the $C^{th}$ chemical and the $s^{th}$ slit can be expressed as its Taylor function expansion around the mid-point of the slit: $A_{CS}=a_{0_{CS}}+a_{1_{CS}}x(t)+a_{2_{CS}}x^2(t)+a_{3_{CS}}x^3(t)+a_{4_{CS}}x^4(t)+a_{5_{CS}}x^5(t)+a_{6_{CS}}x^6(t)+a_{7_{CS}}x^7(t)$. Here, $x(t)$ = Amplitude*$\sin(\omega_0 t)$. The weighting function W can be expressed as $W=k_0+k_1 \sin(\omega_0 t)+k_2 \sin(2\omega_0 t)+k_3 \sin(3\omega_0 t)+k_4 \sin(4\omega_0 t)+k_5 \sin(5\omega_0 t)+k_6 \sin(6\omega_0 t)+k_7 \sin(7\omega_0 t)$. Because $\int \sin(n\omega_0 t) \sin(m\omega_0 t)=0$ unless m=n, very few terms in the product survive.

Figure 5:
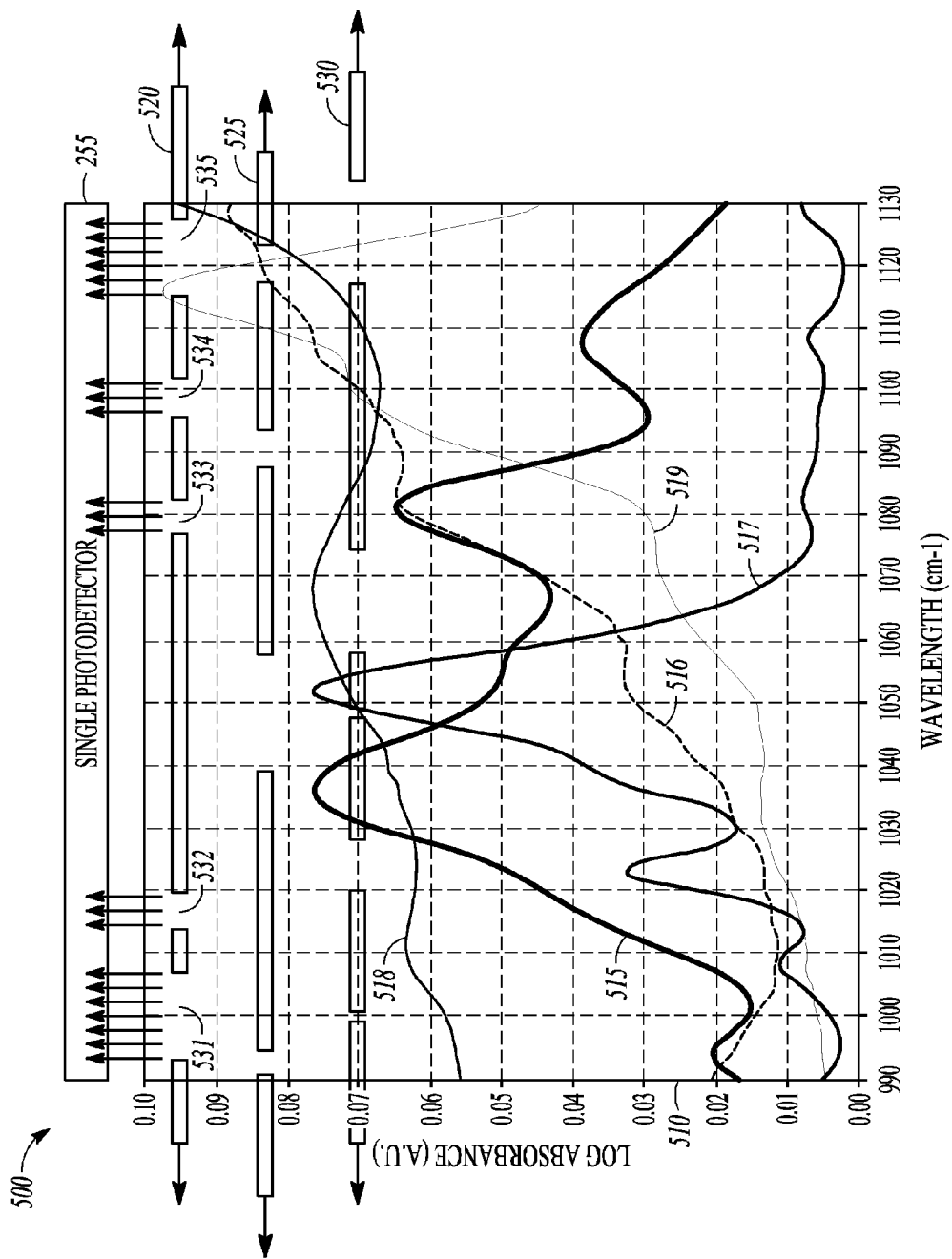
FIG. 5 is a schematic diagram illustrating the spectral response of multiple different gases according to an example embodiment.

Because of spectral smear, the contributions of the sin$(n\omega_0)$ terms diminish rapidly as n increases. The Weighting function brings a tremendous flexibility to provide orthogonality, despite processing and packaging variabilities FIG. 5 is a schematic diagram 500 illustrating a graph showing the spectral response of five different gases, 515, 516, 517, 518, and 519. Three different coded filters 520, 525, and 530 are shown corresponding to the detection of the same gas, 515. The filters may be used separately, or in different lanes in one embodiment. Filter 520 contains five slits 531, 532, 533, 534 and 535. The positions and widths of the filters are designed to detect species 515, while not allowing an AC signal from any of the other gases. Filter 520 results in the signal from gas 515 responding in phase with the oscillating frequency, f0, sometimes referred to as $\omega$. Filter 525 results in an out of phase response at $\omega$. Filter 530 results in an in-phase response at $2\omega$. Thus each filter detects gas 515 and excludes the other gases that are not of interest utilizing different algorithms to sort out the response due to gas 515 from the responses of the other gases.

Figure 6:
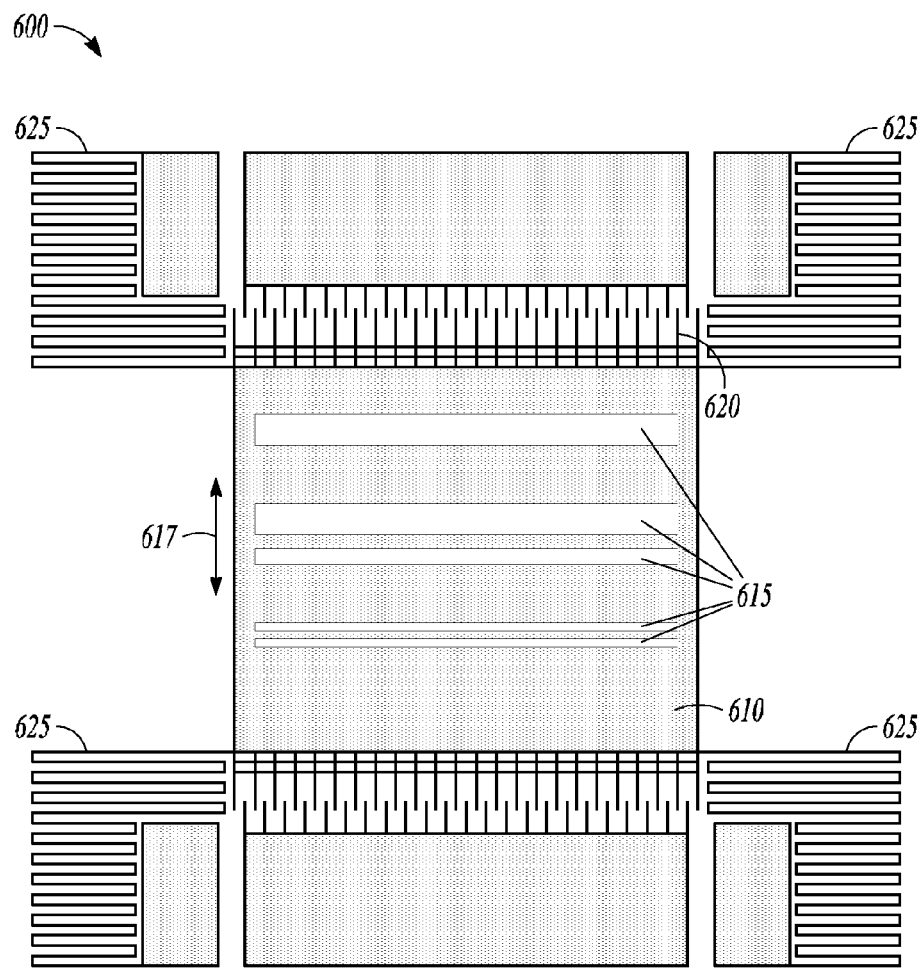
FIG. 6 is a top view representation of a coded filter as part of a microelectromechanical oscillator according to an example embodiment.

FIG. 6 is a top view representation of a coded filter 600 as part of a microelectromechanical oscillator. The filter 600 includes a proof mass 610 that contains multiple slits indicated at 615. The proof mass includes interdigitated electromagnetic drive fingers 620 to provide force to cause oscillation of the proof mass 610 in a direction illustrated at 617, transverse to the spectra to be detected. The proof mass 610 is supported by springs 625. The mass of the proof mass in conjunction with a spring constant of the springs 625 help define a resonant frequency of the proof mass. In various embodiments, the oscillator has a resonant frequency between 50 to 10000 Hertz. In further embodiments, the resonant frequency may be less than 50 or more than 10000 Hertz.

In further embodiments, the coded filter may be moved by one or more of many different types of mechanisms, including electromagnetic actuators. The speed and frequency of the movement may vary significantly, from less than one hertz to many thousands of hertz or higher, provided resulting AC signals can be detected and processed.

The controller may be used to drive the oscillator in some embodiments. A PLL (Phase Locked Loop) may be used to drive the comb oscillator at its resonant frequency. This determines $\omega_0$. A value $\alpha_0$ may be selected to set the overall physical amplitude of the comb driven coded filters. Use $\omega_0$ as the clock frequency for a DDS (Direct Digital Synthesizer), the detection electronics, and the analog to digital converter in the controller.

Circuit Option #1: Select calibration coefficients $k_0$-$k_5$ to weight the various harmonics components of the detection circuit. This enables a high degree of orthogonalization of the signal-of-interest to each spectral interferrant. Amplify the output signal from the DES system using a high-gain TIA (Trans-Impedance Amp). Differentially compare it to the DDS waveform using an adder. Convert to digital, and output the signal to a microprocessor. The control circuit used to drive the coded filter at resonance is similar to the circuit used in high-precision MEMS gyros. A coherent source and post-detection signal processing may be used. Signals and noise levels in the picoWatt range may be handled. Integrate until S/N>>1.

Circuit Option #2: Process the raw data from the DES digitally. Add jitter to compensate LSB errors. This circuit option has more flexibility in dealing with the amplitude of the data, but may have less precision in dealing with timing (spectral resolution) of the data.

Figure 7:
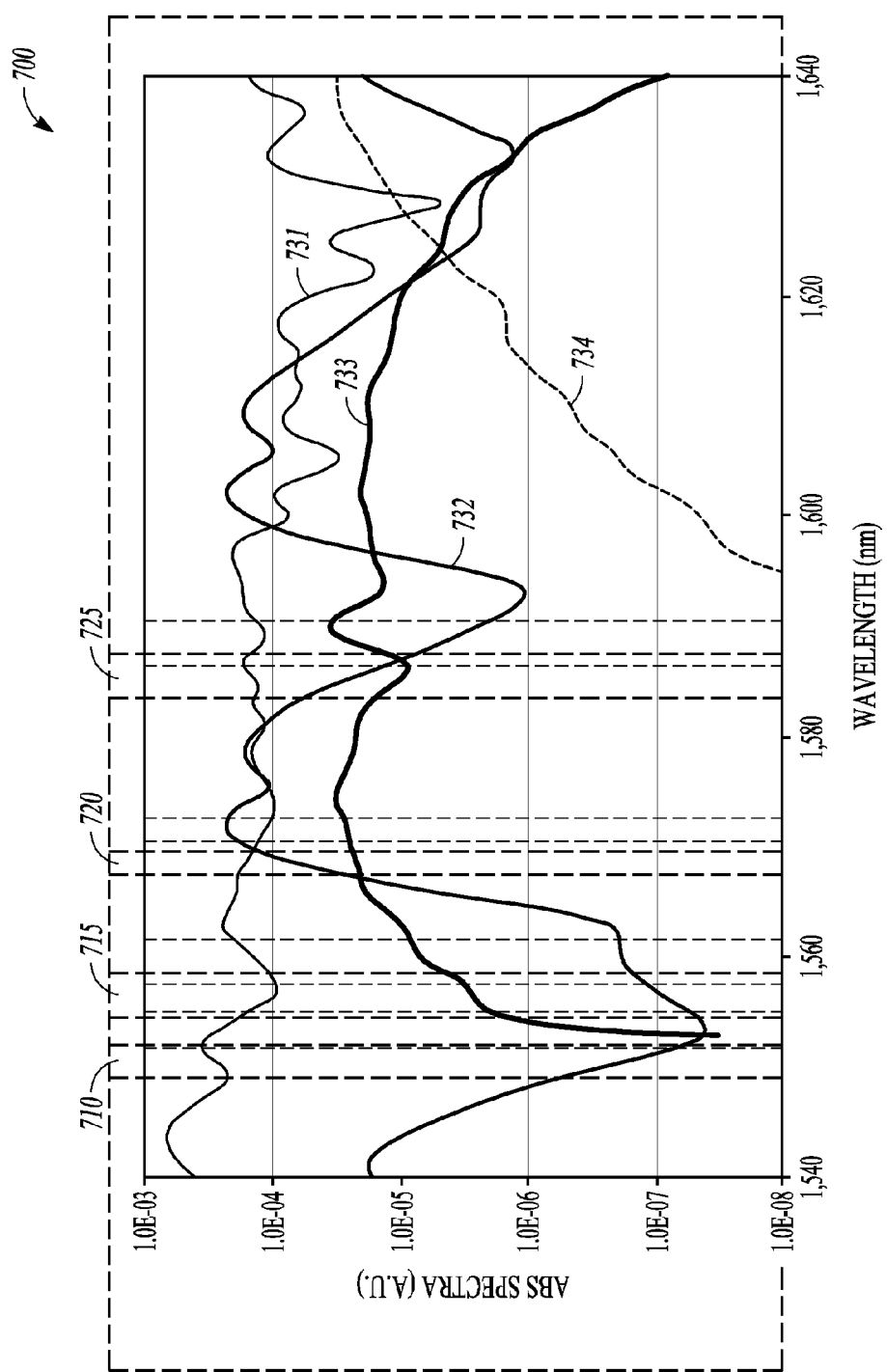
FIG. 7 is a schematic diagram of a four slit coded filter designed to detect a gas according to an example embodiment.

A specific example coded filter is illustrated at 700 in FIG. 7. The filter 700 includes four slits, 710, 715, 720 and 725 arranged to detect $H_2S$. In one embodiment, the path length between the light source and the detector is approximately 20 meters. Spectral signatures reaching the coded filter have approximately $10^{-1}$ cm of Gaussian smear. Several gases are present, as illustrated at 731 $H_2O$ 4%, 732 $CO_2$ 390 ppm, 733—$H_2S$ 1 ppm, and 734 $CH_4$ 1.79 ppm. Several species, such as N2, O2, Ar, Ne, He, H2, and C=2-20 alkanes are not spectrally significant in the wavelength range of interest.

Slit 710 begins at 1549.00 nm and has a width of 3 nm. Slit 715 begins at 1554.50 nm and has a width of 4 nm. Slit 720 begins at 1567.5 nm and has a width of 2 nm. Slit 725 begins at 1583.5 nm and has a width of 4 nm. Each oscillation moves the slits 3 nm in both directions from nominal. This is just one example. The arrangement of slits, widths of various slits, and length of movement of the coded filter may vary from embodiment to embodiment.

The design of a coded filter may be done in many different ways. The use of spreadsheets with spectral information for multiple expected gases may be used to help identify positions and widths of slits. In some cases, the design may involve some trial and error, but may also be keyed off understanding the spectral responses of a finite number of gases, including the gas of interest. Noting the portions of the spectra of each gas where changes occur can quickly narrow the locations of potential slots. Utilizing multiple lanes can further reduce the complexity of design, as each lane may be formed to reject fewer spectral responses of gases, while allowing detection of a gas of interest.

Figure 8:
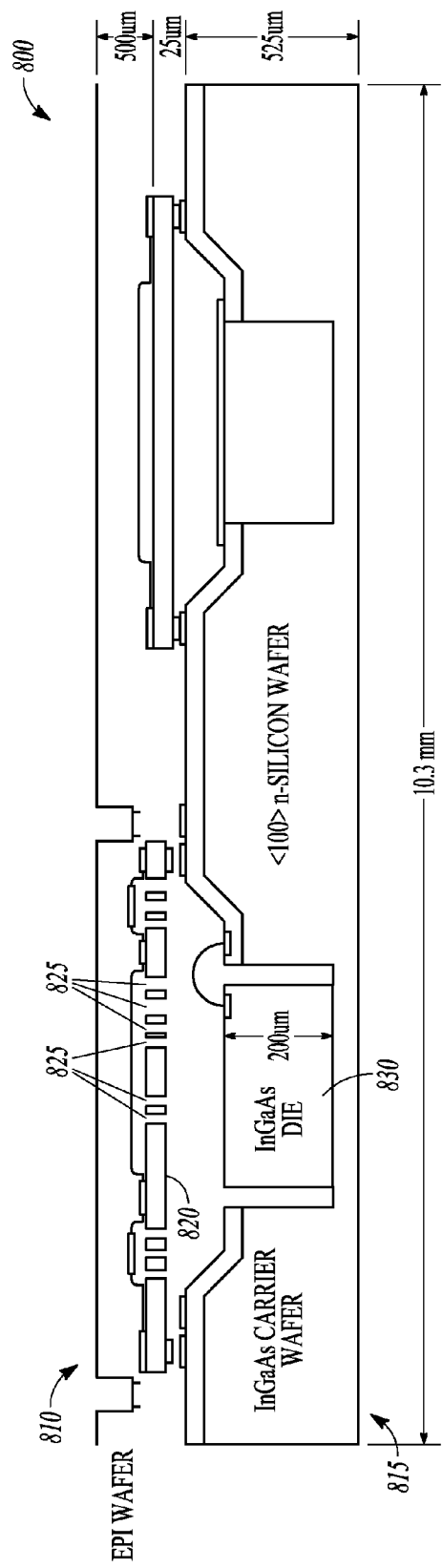
FIG. 8 is a cross section view of a multiple wafer device for detecting gas according to an example embodiment.

FIG. 8 is a cross section view of a device 800 that includes a first wafer 810 coupled to a second wafer 815. This view is not necessarily to scale. First wafer 810 may include a coded filter 820 having slits 825. The filter 820 may be a proof mass of a microelectromechanical oscillator formed from and supported by first wafer 810. The coded filter 820 may be positioned over an InGaAs photo detector 830 supported by the second wafer 815. The second wafer may be a <100> oriented n-silicon wafer in one embodiment. Any type of photodetector capable of detecting a desired spectrum of light may be used in various embodiments. Similarly, any type of actuator may be used to provide motion for the coded filter.

Figure 9:
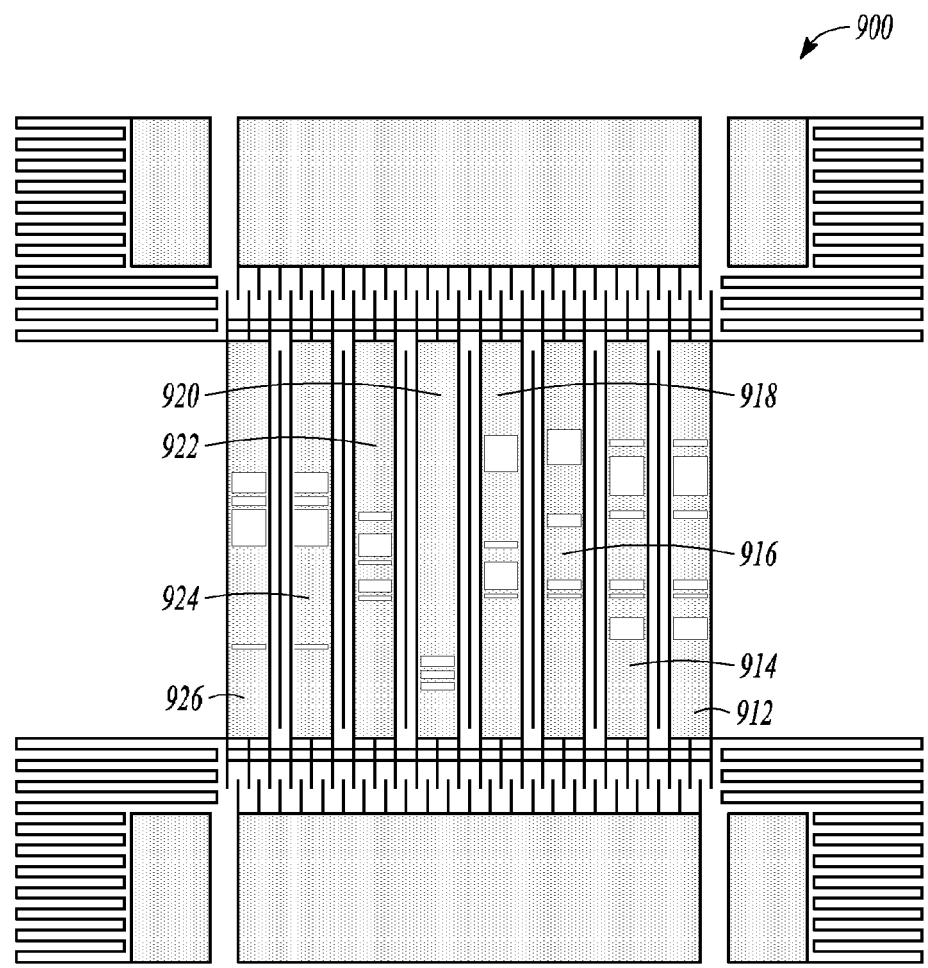
FIG. 9 is a schematic view of a multiple lane filter according to an example embodiment.

FIG. 9 illustrates a multiple lane coded filter 900 designed for detection of Sarin gas in air. There are eight lanes illustrated at 912, 914, 916, 918, 920, 922, 924, and 926. Each lane has a corresponding photo detector located beneath it, and represented by the same reference number, but not visible in this view. The lanes are formed in a proof mass of a microelectromechanical oscillator as previously described. Filter 900 is designed knowing in advance the spectra of all of the gas species likely to be present. In one embodiment, the gas is Sarin, but may also be GB, GD, and other undesirable gases that are crucial to detect prior to being exposed to humans. Gases that the filter is designed to not respond to include $H_2O$, $CO_2$, $O_3$, $CH_4$, and others.

Figure 10:
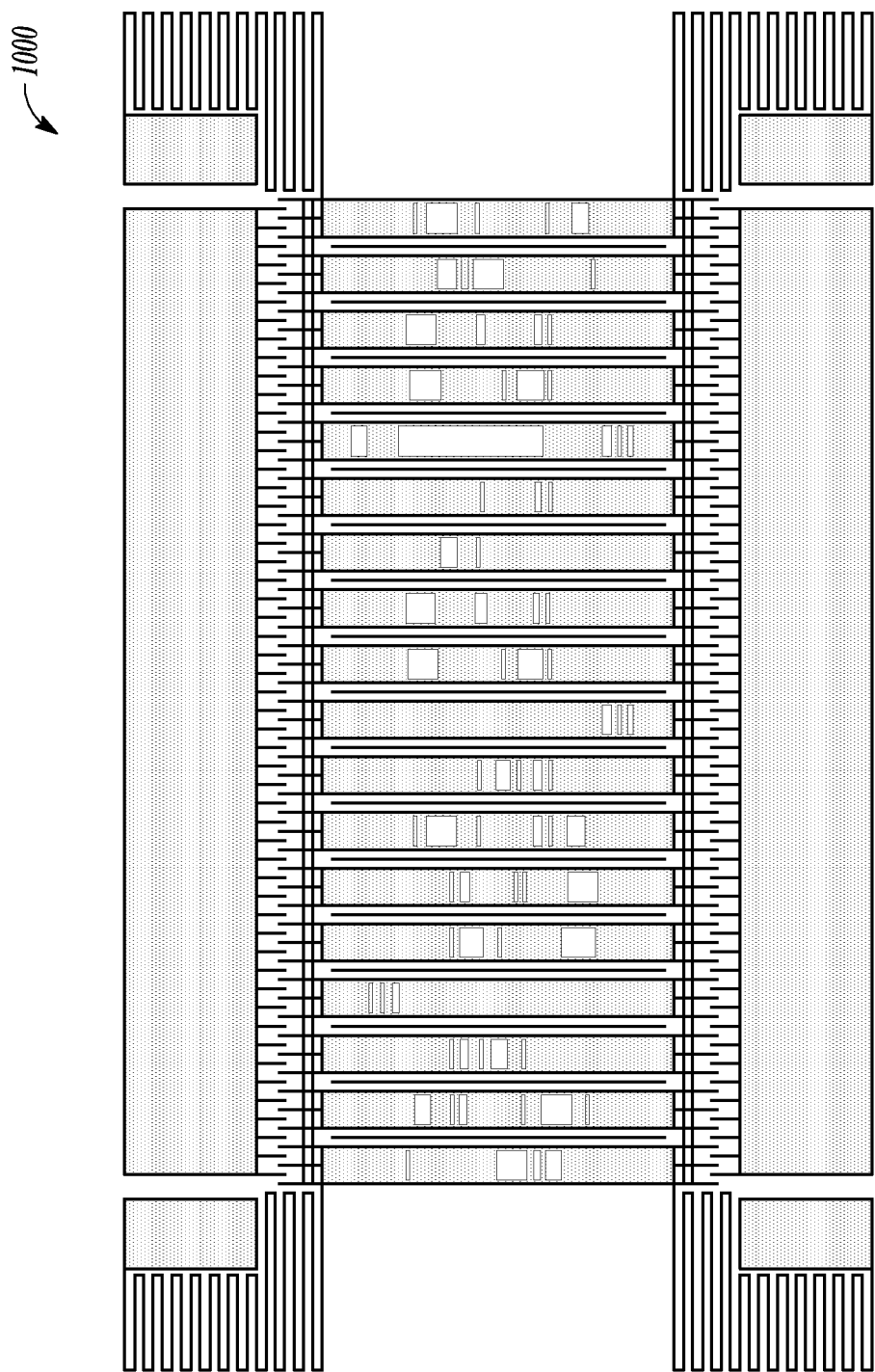
FIG. 10 is a schematic view of a further multiple lane filter according to an example embodiment.

FIG. 10 illustrates a multiple lane coded filter 1000 having eighteen lanes. This type of filter may be used to detect one or more desired gases. One approach of designing a filter with this many lanes is to work from knowledge of what the problem is not. Such gases might include $H_2O$, $CO_2$, $CF_4$, and others. The coded filters may be dynamically orthogonal to several of the most common gases. A lookup table of 1000 spectra of interest may be utilized to design the slits. Each lane will have a known response to each of the spectra. The residuals from each of the coded filters may be used as fitting coefficients to uniquely identify a blend of gases.

Figure 11:
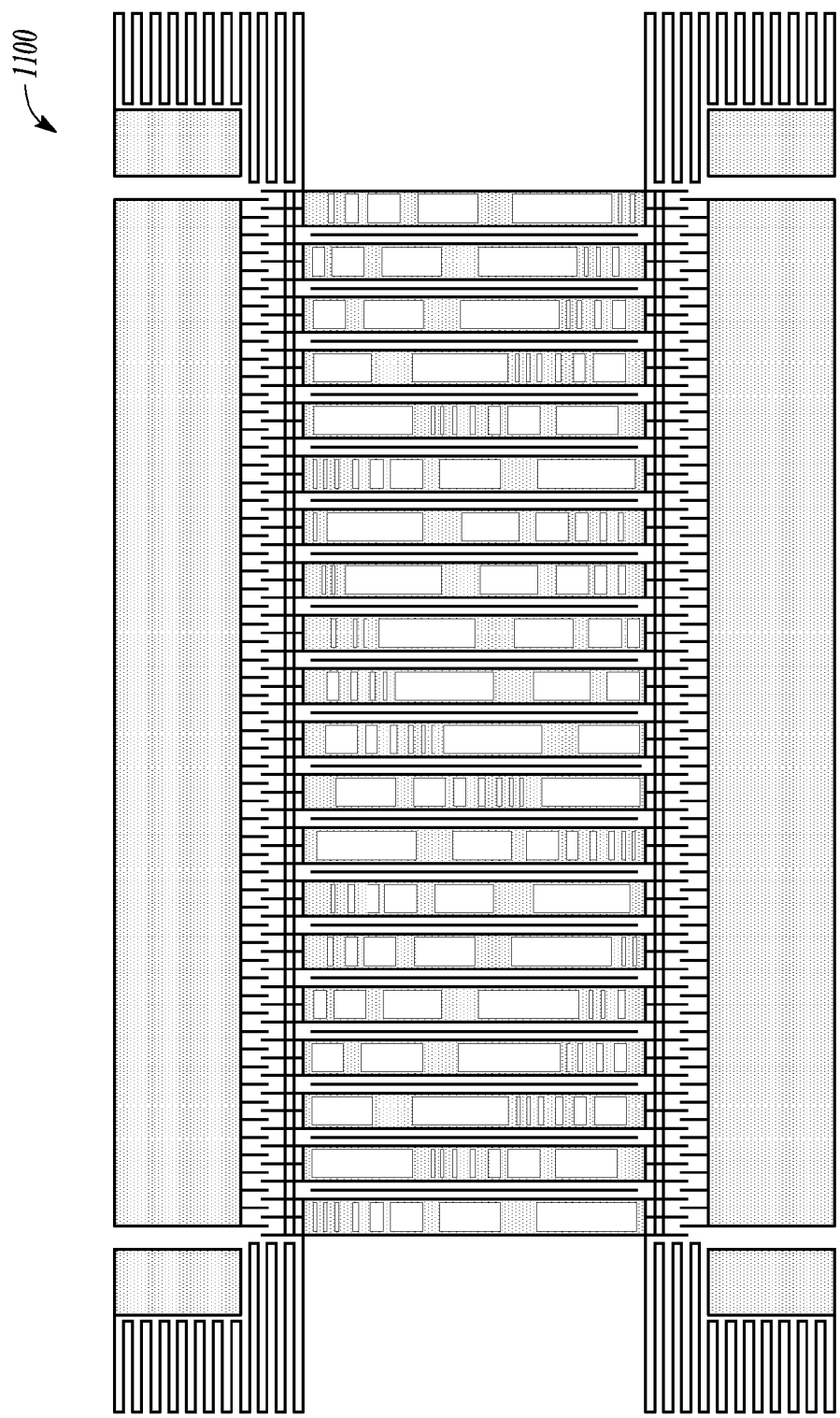
FIG. 11 is a schematic view of yet a further multiple lane filter according to an example embodiment.

FIG. 11 illustrates a filter 1100 designed from the knowledge that the spectral response of a gas of interest may not be known at the time the filter is designed. The filter contains about 20 different lanes to form an infinitely flexible set of Hadamard-like coded filters that can be software weighted in the field. Each coded filter separates different portions of the spectrum into n segments, where n=1, 2, 3, . . . to approximately 100. Approximately seven Fourier harmonics from each coded filter may be weighted differently, with weighting coefficients that can be set in the field. The net effect is approximately 140 degrees of freedom, with plenty of parameter space in which to find orthogonality. Orthogonality to an arbitrary set of spectral waveforms (any arbitrary set of gas species) can be achieved by a combination of the signals from the complete set of coded filters. The data may be analyzed by using software supplied weighting coefficients for Taylor-Fourier components together with an overall set of weighting coefficients for each individual coded filter.

Figure 12:
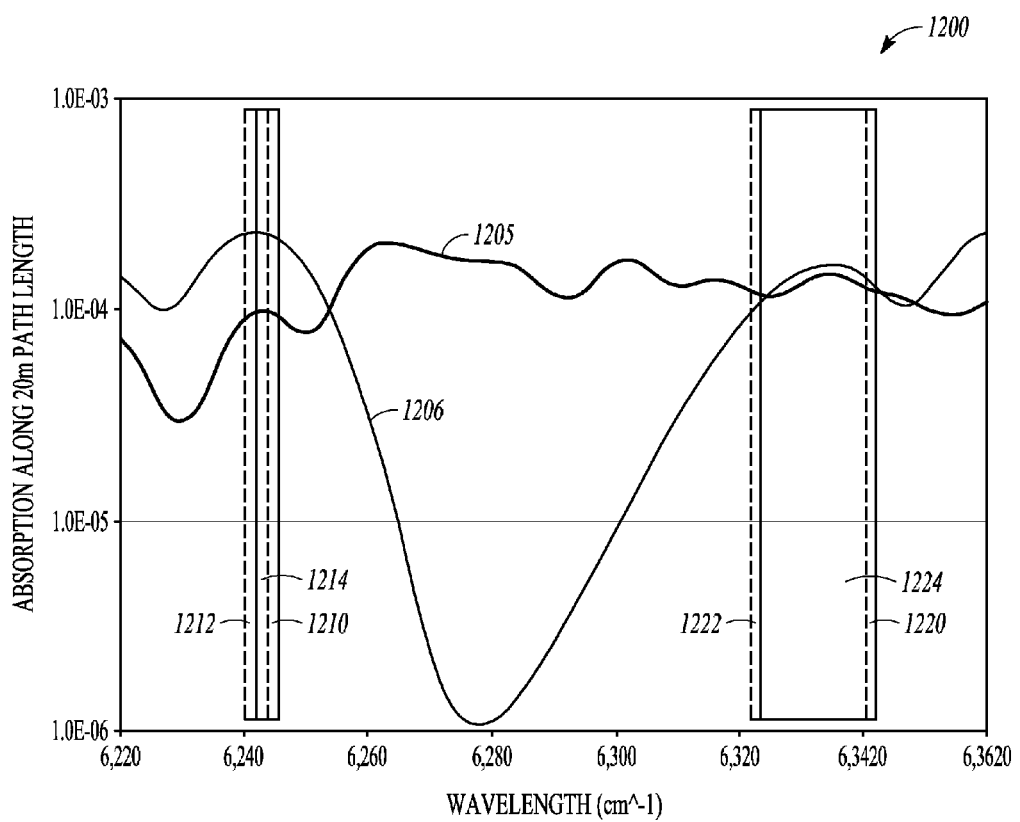
FIG. 12 is a schematic view of a coded filter that is dynamically orthogonal to two common gases not of interest according to an example embodiment.

FIG. 12 illustrates a two slit coded filter 1200 that is dynamically orthogonal to $H_2O$ and $CO_2$, referred to as the big two gases. The two slits are indicated at 1210 and 1220. Slit 1210 moves between positions indicated at 1212 and 1214. Slit 1220 moves between positions indicated at 1222 and 1224, distances that are identical to the distance slit 1210 moves. As the coded filter is dithered back and forth, there is zero AC signal from both $H_2O$ and $CO_2$ no matter how much of each is present.

EXAMPLES

1. A device for detecting gas concentrations comprising:
a movable coded filter;
an optical element positioned to receive gas filtered light and spectrally separate the gas filtered light; and
a photo detector positioned to receive the spectrally separated light through slits in the moveable coded filter to provide an AC signal representative of a selected gas.

2. The device of example 1 wherein the filter comprises an opaque plane having slits.

3. The device of example 2 wherein the slits are positioned on the opaque plane to pass at least two AC components of the spectrally separated light corresponding to a gas not of interest such that the AC components cancel out on the photo detector.

4. The device of example 3 wherein the slits are positioned on the opaque plane to pass at least one AC component of the spectrally separated light corresponding to the selected gas.

5. The device of example 4 wherein a slit in the coded filter corresponding to the AC component of the spectrally separated light corresponding to the selected gas moves about a peak of the selected gas spectra as the coded filter is moved.

6. The device of any of examples 1-5 wherein the coded filter comprises an opaque proof mass of a comb drive microelectromechanical oscillator.

7. The device of example 6 wherein the oscillator has a resonant frequency between 50 to 10000 Hertz.

8. The device of any of examples 1-7 wherein the slits have different widths.

9. The device of any of examples 1-8 wherein the slits are arranged to cancel AC components of the spectrally separated light from at least two gasses not of interest.

10. The device of any of examples 1-9 wherein the coded filter comprises multiple parallel coded filters in a single opaque proof mass and wherein the photodetector comprises a separate photodetector for each of the multiple parallel coded filters.

11. The device of any of examples 1-10 and further comprising a first collimator positioned to collimate light received by the coded filter.

12. The device of example 11 and further comprising a second collimator positioned to collimate light provided to the optical element.

13. The device of any of examples 1-12 and further comprising a processor programmed to add a weighting function at a resonant frequency of the moveable coded filter to compensate for red-blue coded filter mis-alignment.

14. The device of any of examples 1-13 and further comprising a process programmed to add a weighting function at three times a resonant frequency of the moveable coded filter to compensate for slit width errors.

15. A device for detecting gas concentrations comprising:
a movable coded filter having multiple slits in a proof mass;
an optical element positioned to receive gas filtered light and spectrally separate the gas filtered light onto the coded filter wherein spectral bands run in the same direction as the slits, the slits positioned to cancel AC signals corresponding to at least one gas not of interest;
a photo detector positioned to receive the spectrally separated light through the oscillating slits in the moveable coded filter to provide an AC signal representative of a selected gas; and
a controller coupled to receive the AC signal, convert the AC signal to a digital signal, and to correlate an amplitude of the AC signal to a concentration of the selected gas.

16. A method for detecting a gas, the method comprising:
receiving light from a light source through a plume of gas;
spectrally separating the light;
oscillating a coded filter to selectively pass portions of the spectrally separated light onto a single photo detector; and
detecting an AC signal via the single photo detector representative of a gas of interest.

17. The method of example 16 wherein the light is spectrally separated via a diffraction grating.

18. The method of any of examples 16-17 wherein the portions of the spectrally separated light pass through multiple slits of the coded filter such that AC components of light from at least one gas not of interest cancel each other and wherein AC component of light from the gas of interest add to each other.

19. The method of example 18 wherein the slits of the coded filter are configured to cancel AC components of multiple gases not of interest.

20. The method of any of examples 16-19 wherein the AC signal at a frequency of twice the frequency of oscillation of the coded filter is representative of the gas of interest.

Although a few embodiments have been described in detail above, other modifications are possible. For example, the logic flows depicted in the figures do not require the particular order shown, or sequential order, to achieve desirable results. Other steps may be provided, or steps may be eliminated, from the described flows, and other components may be added to, or removed from, the described systems. Other embodiments may be within the scope of the following claims.

The invention claimed is:

1. A device for detecting gas concentrations comprising:
a movable coded filter;
an optical element positioned to receive gas filtered light and spectrally separate the gas filtered light; and
a photo detector positioned to receive the spectrally separated light through slits in the moveable coded filter to provide an AC signal representative of a selected gas, wherein the slits are positioned to pass at least two AC components of the spectrally separated light corresponding to a gas not of interest such that the AC components cancel out on the photo detector.

2. The device of claim 1 wherein the coded filter comprises an opaque plane having slits.

3. The device of claim 2 wherein the slits are positioned on the opaque plane to pass at least one AC component of the spectrally separated light corresponding to the selected gas.

4. The device of claim 3 wherein a slit in the coded filter corresponding to the AC component of the spectrally separated light corresponding to the selected gas moves about a peak of the selected gas spectra as the coded filter is moved.

5. The device of claim 1 wherein the coded filter comprises an opaque proof mass of a comb drive microelectromechanical oscillator.

6. The device of claim 5 wherein the oscillator has a resonant frequency between 50 to 10000 Hertz.

7. The device of claim 1 wherein the slits have different widths.

8. The device of claim 1 wherein the slits are arranged to cancel AC components of the spectrally separated light from at least two gasses not of interest.

9. The device of claim 1 wherein the coded filter comprises multiple parallel coded filters in a single opaque proof mass and wherein the photodetector comprises a separate photodetector for each of the multiple parallel coded filters.

10. The device of claim 1 and further comprising a first collimator positioned to collimate light received by the coded filter.

11. The device of claim 10 and further comprising a second collimator positioned to collimate light provided to the optical element.

12. The device of claim 1 and further comprising a processor programmed to add a weighting function at a resonant frequency of the moveable coded filter to compensate for red-blue coded filter mis-alignment.

13. The device of claim 1 and further comprising a process programmed to add a weighting function at three times a resonant frequency of the moveable coded filter to compensate for slit width errors.

14. A device for detecting gas concentrations comprising:
a movable coded filter having multiple slits in a proof mass;
an optical element positioned to receive gas filtered light and spectrally separate the gas filtered light onto the coded filter wherein spectral bands run in the same direction as the slits, the slits positioned to cancel AC signals corresponding to at least one gas not of interest;
a photo detector positioned to receive the spectrally separated light through the oscillating slits in the moveable coded filter to provide an AC signal representative of a selected gas; and
a controller coupled to receive the AC signal, convert the AC signal to a digital signal, and to correlate an amplitude of the AC signal to a concentration of the selected gas.

15. A method for detecting a gas, the method comprising:
receiving light from a light source through a plume of gas;
spectrally separating the light;
oscillating a coded filter to selectively pass portions of the spectrally separated light onto a single photo detector; and
detecting an AC signal via the single photo detector representative of a gas of interest, wherein the portions of the spectrally separated light pass through multiple slits of the coded filter such that AC components of light from at least one gas not of interest cancel each other and wherein AC component of light from the gas of interest add to each other.

16. The method of claim 15 wherein the light is spectrally separated via a diffraction grating.

17. The method of claim 15 wherein the slits of the coded filter are configured to cancel AC components of multiple gases not of interest.

18. The method of claim 15 wherein the AC signal at a frequency of twice the frequency of oscillation of the coded filter is representative of the gas of interest.

* * * * *